(12) United States Patent
Ogawa et al.

(10) Patent No.: US 9,157,870 B2
(45) Date of Patent: Oct. 13, 2015

(54) PATTERN TEST APPARATUS

(71) Applicants: NuFlare Technology, Inc., Numazu-shi (JP); KABUSHIKI KAISHA TOSHIBA, Minato-ku (JP)

(72) Inventors: Riki Ogawa, Kawasaki (JP); Masatoshi Hirono, Yokohama (JP)

(73) Assignees: NuFlare Technology, Inc., Numazu-shi (JP); KABUSHIKI KAISHA TOSHIBA, Minato-ku (JP)

( * ) Notice: Subject to any disclaimer, the term of this patent is extended or adjusted under 35 U.S.C. 154(b) by 107 days.

(21) Appl. No.: 13/956,708

(22) Filed: Aug. 1, 2013

(65) Prior Publication Data
US 2014/0055780 A1    Feb. 27, 2014

(30) Foreign Application Priority Data

Aug. 21, 2012  (JP) ................................ 2012-182228

(51) Int. Cl.
*G01N 21/00*  (2006.01)
*G01N 21/956*  (2006.01)

(52) U.S. Cl.
CPC ........ *G01N 21/956* (2013.01); *G01N 21/95607* (2013.01); *G01N 2021/95676* (2013.01)

(58) Field of Classification Search
CPC . G01N 21/956; G01N 21/9501; G01N 21/21; G01N 21/95607
USPC ............ 356/237.1–237.5, 364–369, 445–448
See application file for complete search history.

(56) References Cited

U.S. PATENT DOCUMENTS

| | | | | |
|---|---|---|---|---|
| 5,418,380 | A * | 5/1995 | Simon et al. | 250/550 |
| 6,304,330 | B1 * | 10/2001 | Millerd et al. | 356/521 |
| 7,859,656 | B2 | 12/2010 | Uto et al. | |
| 2004/0033426 | A1 * | 2/2004 | Den Boef et al. | 430/22 |
| 2007/0070336 | A1 * | 3/2007 | Maeda et al. | 356/237.2 |

(Continued)

FOREIGN PATENT DOCUMENTS

| | | |
|---|---|---|
| JP | 3610837 | 10/2004 |
| JP | 2004-361645 | 12/2004 |

(Continued)

OTHER PUBLICATIONS

Combined Taiwanese Office Action and Search Report issued Nov. 10, 2014 in Taiwanese Patent Application No. 102127774 (with English language translation).
Japanese Office Action issued Sep. 10, 2013, in Japan Patent Application No. 2012-182228 (with English translation).
U.S. Appl. No. 14/153,199, filed Jan. 13, 2014, Ogawa, et al.
Office Action issued Sep. 26, 2014 in Korean Patent Application No. 10-2013-0097287 (with English language translation).

*Primary Examiner* — Hoa Pham
(74) *Attorney, Agent, or Firm* — Oblon, McClelland, Maier & Neustadt, L.L.P.

(57) ABSTRACT

According to one embodiment, a pattern test apparatus includes a light source configured to apply test light to a test sample, a polarizing beam splitter which reflects or transmits the test light, an imaging device which receives light which has been reflected by the test sample and transmitted through or reflected by the polarizing beam splitter, an optical system which forms a Fourier transform plane of the test sample between the test sample and the polarizing beam splitter, and a polarizing controller disposed in the Fourier transform plane. The polarizing controller includes a first region which lets the test light through, and a second region which is greater than the first region and lets the light reflected by the test sample through, and the each regions have different retardation quantities.

8 Claims, 4 Drawing Sheets

(56) References Cited

U.S. PATENT DOCUMENTS

2007/0177136 A1* 8/2007 Nakano et al. ............ 356/237.2
2010/0014083 A1* 1/2010 Ueno et al. .................. 356/364
2012/0019816 A1 1/2012 Shibata et al.
2012/0050518 A1 3/2012 Miyata

FOREIGN PATENT DOCUMENTS

| JP | 3918840 | 2/2007 |
| JP | 3936959 | 3/2007 |
| KR | 10-2008-0094291 A | 10/2008 |
| TW | 201209392 A1 | 3/2012 |

* cited by examiner

PATTERN TEST APPARATUS

CROSS-REFERENCE TO RELATED APPLICATIONS

This application is based upon and claims the benefit of priority from Japanese Patent Application No. 2012-182228, filed Aug. 21, 2012, the entire contents of which are incorporated herein by reference.

FIELD

Embodiments described herein relate generally to a pattern test apparatus, which optically tests defects in a pattern of a test sample.

BACKGROUND

In pattern test apparatuses, test light is required to be of sufficient amount to test pattern defects in a test sample such as a photomask, in which a minute pattern is formed. Thus, a method of improving the lighting efficiency by a combination of a quarter-wave plate and a polarizing beam splitter (PBS) is used, as a coaxial episcopic illumination method.

Specifically, S-polarized light from the light source is reflected by the PBS, converted into circularly polarized light by a quarter-wave plate, and applied to the surface of the mask. Then, the light reflected from the surface of the mask is converted into P-polarized light by the quarter-wave plate, and made incident on the PBS. The light which has transmitted through the PBS is detected by a sensor.

In the above method, however, when the pattern formed on the photomask has a periodic structure which is shorter than the wavelength of the test light, the polarized state of the light reflected from the surface of the mask is changed by the influence of form birefringence, in which the refractive index differs according to the orientation of the electric field of the incident light. Thus, the light reflected from the surface of the mask cannot be efficiently transmitted through the PBS. Therefore, a reduction in the amount of light for pattern testing is inevitable, leading to reduced test accuracy.

DETAILED DESCRIPTION

In general, according to one embodiment, a pattern test apparatus, which tests pattern defects by using a pattern image obtained by applying light to a test sample, comprises: a light source configured to apply test light of a predetermined wavelength to the test sample; a polarizing beam splitter which reflects or transmits the light from the light source, and guides the light onto the test sample; an imaging device which receives light which has been reflected by the test sample and transmitted through or reflected by the polarizing beam splitter; an optical system which forms a Fourier transform plane of the test sample between the test sample and the polarizing beam splitter; and a polarizing controller disposed in the Fourier transform plane. The polarizing controller includes a first region which lets the test light through, and a second region which has an area greater than that of the first region and lets the light reflected by the test sample through, and the first region and the second region have different retardation quantities.

A pattern test apparatus according to embodiments will be explained hereinafter with reference to drawings.

(First Embodiment)

Figure 1:
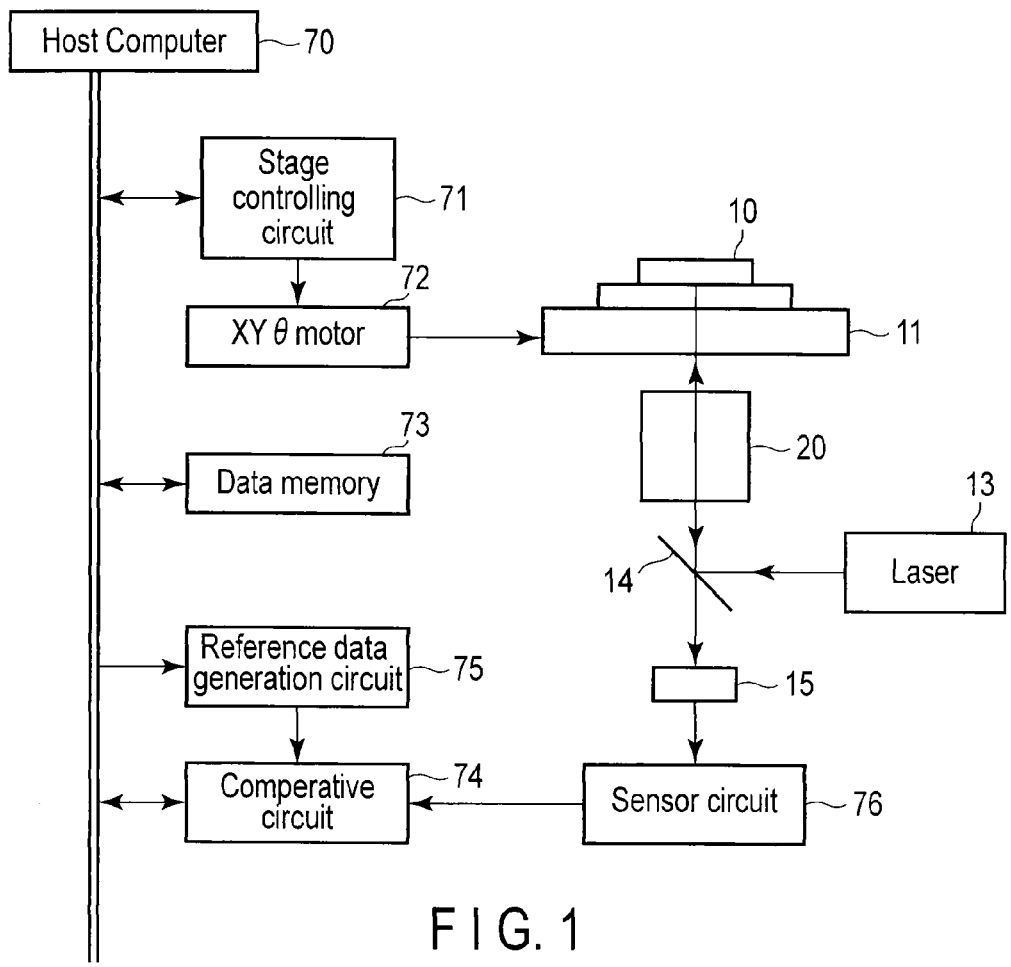
FIG. 1 is a diagram illustrating a basic structure of a pattern test apparatus according to a first embodiment.

FIG. 1 is a diagram illustrating a basic structure of a pattern test apparatus for a photomask, according to a first embodiment. The present embodiment shows an example of a structure of a pattern test apparatus, which tests a pattern by comparing design data of a photomask used for manufacturing LSIs with measured data thereof.

Figure 2:
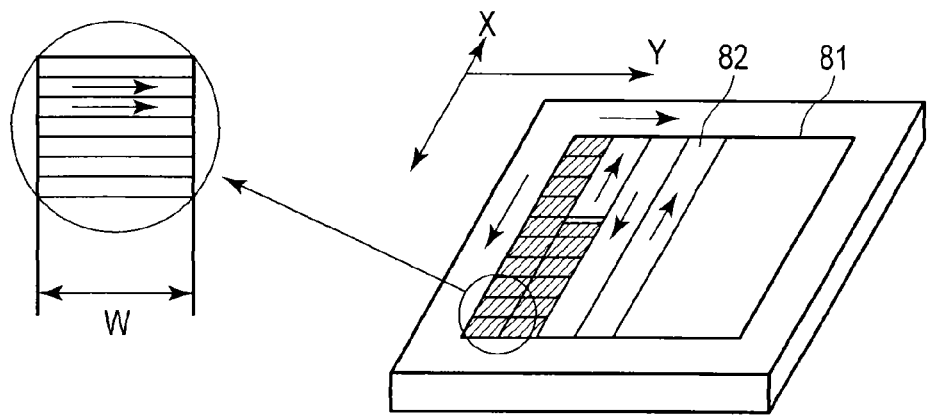
FIG. 2 is a schematic diagram for explaining test stripes of a photomask.

In the apparatus, a test region 81 in a pattern formed on a photomask 10 is divided into rectangular test stripes 82 having a width of W, as illustrated in FIG. 2. The mask 10 is placed on an XYθ table 11 illustrated in FIG. 1, such that the divided test stripes 82 are continuously scanned, and test is carried out while a stage of one axis thereof is continuously moved. When testing of the stripe ends, step movement is executed with a stage of another axis to observe the next stripe.

The photomask 10 is placed on the XYθ table 11. The table 11 can be moved by a table controlling circuit 71 and an XYθ motor 72, under the control of a host computer 70.

The pattern formed on the photomask 10 is irradiated with light by a light source 13, such as a DUV (ultraviolet) laser. The light reflected by the photomask 10 is made incident on a photodiode array (imaging sensor) 15 through an optical system 20. Part of a rectangular region of the pattern, which has been virtually divided as illustrated in FIG. 2, is enlarged and formed as an optical image on the photodiode array 15. The pattern image formed on the photodiode array 15 is subjected to photoelectric conversion by the photodiode array 15, and subjected to analog-to-digital conversion by a sensor circuit 76. The measured image data output from the sensor circuit 76 is transmitted to a comparison circuit 74.

On the other hand, the design data used when the pattern of the photomask 10 was formed is read from a data memory 73, such as a magnetic disk or a semiconductor memory, into a reference data generation circuit 75 through a controlling computer 70. In the reference data generation circuit 75, the read design data is converted into binary or multi-valued design image data.

The comparison circuit 74 compares the measured image data with the design image data in accordance with a proper algorithm, and determines that there is a defect when they do not agree. Specifically, pattern defects of the photomask 10 are detected by die-to-database method.

Figure 3:
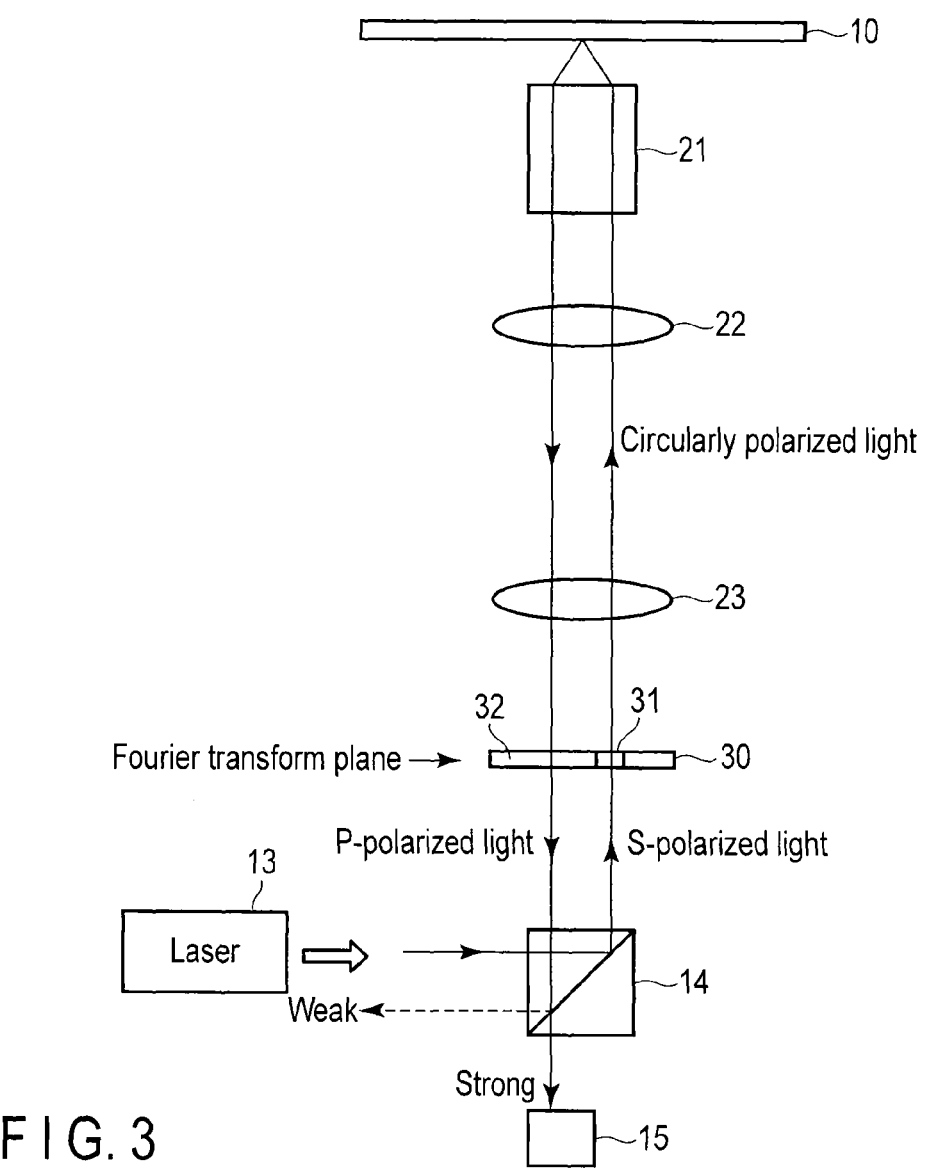
FIG. 3 is a diagram illustrating an optical structure of the pattern test apparatus according to the first embodiment.

FIG. 3 is a diagram illustrating an optical structure of the pattern test apparatus according to the first embodiment. The structure is an example of testing by means of circularly polarized light, and using a segmented wave plate in a pupil or pupil conjugate position of an objective lens.

The optical system 20 including an objective lens 21 and relay lenses 22 and 23 is provided to face a surface of the photomask 10 serving as the test sample.

Suppose that the light to light up the photomask 10 is emitted from the laser light source 13, and adjusted to have S-polarized light with respect to a reflecting surface of the polarizing beam splitter. The first linearly polarized light (S-polarized light) is reflected by the polarizing beam splitter (PBS) 14, and obliquely applied to the surface of the photomask 10 by the optical system 20. The light reflected by the surface of the photomask 10 is extracted by the optical system 20, and applied to the photodiode array 15 through the PBS 14.

In the optical system 20, a Fourier transform plane, which is a focal plane of the optical system for the surface of the photomask 10, is formed between the photomask 10 and the PBS 14. A polarizing controller 30 is placed in the Fourier transform plane.

Specifically, the relay lens 23 is placed in a position closer to the PBS 14, and the relay lens 22 is placed in a position closer to the objective lens 21. They are placed such that the pupil position of the objective lens 21 corresponds to the focal position of the relay lens 22, and the other focal position of the relay lens 22, which is located on a side opposite to a side facing the objective lens, corresponds to the focal position of the relay lens 23. In addition, the polarizing controller 30 is placed in the other focal position of the relay lens 23, which is located on a side opposite to a side facing the relay lens 22. Thereby, the Fourier plane of the photomask surface is formed in the position of the polarizing controller 30.

Figure 4:
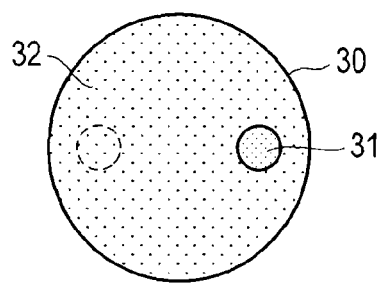
FIG. 4 is a plan view illustrating a structure of a polarizing controller used for the pattern test apparatus of FIG. 3.

The polarizing controller 30 is a disk, and disposed in line with the optical axis of the optical system 20. As illustrated in FIG. 4, the polarizing controller 30 includes a circular first region 31, and a second region 32 which is the other part of the polarizing controller 30. The first region 31 is located in a position shifted from the optical axis of the optical system 20, and illumination light passes through the first region 31.

The first region 31 is a quarter-wave plate, and the second region 32 is a birefringent device which has retardation different from that of the quarter-wave plate. More specifically, the second region 32 removes the influence of birefringence in the light reflected by the photomask 10, and converts the reflected light into P-polarized light which easily passes through the PBS 14. For example, crystal is used as the birefringent device, and a desired retardation is achieved by adjusting the thickness of the substrate thereof. Both a quarter-wave plate and a half-wave plate may be placed at adjusted angles, to provide desired retardations in desired directions.

Specifically, the retardation of the first region 31 of the polarizing controller 30 is 90°, and the retardation of the second region 32 is obtained by shifting the retardation from 90° by the change in the polarized state obtained by birefringence in the photomask 10. In the polarizing controller 30, the first region 31 being a quarter-wave plate occupies only a part of the polarizing controller 30. The second region 32, which occupies the most part of the polarizing controller 30, is a birefringent device different from the quarter-wave plate.

Since the illumination light from the light source 13 is a minute spot light, and passes through the first region 31, which has a small area, in a sufficiently large amount. On the other hand, the light reflected from the photomask 10 basically passes through a position (part enclosed by a broken line in FIG. 4) shifted from the region, through which the illumination light passes. Since the reflected light includes not only zero-order diffracted light but also high-order diffracted light, the reflected light spreads over a range wider than the illumination light passage region. Thus, a desired wave plate (with a retardation obtained by shifting the retardation from 90° by the change in the polarized state obtained by birefringence in the photomask 10) is used for all the region (second region 32) other than the illumination light passage region, and thereby the reflected light going toward the sensor can be efficiently converted to P-polarized light.

Since a quarter-wave plate is provided in the illumination light passage region, the illumination light is changed into circularly polarized light, and applied to the photomask 10 in an oblique direction. Although the reflected light from the photomask 10 is extracted by the optical system 20, the position thereof is dislocated in the Fourier transform plane. Then, the reflected light is changed into P-polarized light by passing through the second region 32 of the polarizing controller 30, passes through the PBS 14 and is detected by the photodiode array 15. The second region 32, through which the light reflected from the photomask 10 passes, is not the same as the wave plate of the first region which lets the test light pass through, but cancels the influence of form birefringence in the surface of the photomask 10, and changes the reflected light into P-polarized light. Thus, the amount of light which passes through the PBS 14 is sufficiently large.

As described above, according to the present embodiment, the polarizing controller 30 is provided in the Fourier transform plane of the photomask 10, and the reflected light from the photomask 10 passes through a wave plate different from a wave plate on the incident side. Thus, the light reflected from the photomask 10 can be efficiently changed into P-polarized light. Therefore, the amount of light which passes through the PBS 14 is increased, and the amount of light received by the sensor increases.

Thus, even when the test pattern has a periodic structure smaller than the wavelength, it is possible to prevent a reduction in the amount of light because of the influence of form birefringence, and so improve the test accuracy. In addition, since the polarizing controller 30 is provided in the Fourier transform plane of the photomask 10, even the first region 31 with a small area can guide test light of sufficient amount to the mask. Besides, the reflected light from the photomask 10 is extracted through the second region 32 having a large area. This structure enables pattern defect test with good light use efficiency.

(Second Embodiment)

Figure 5:
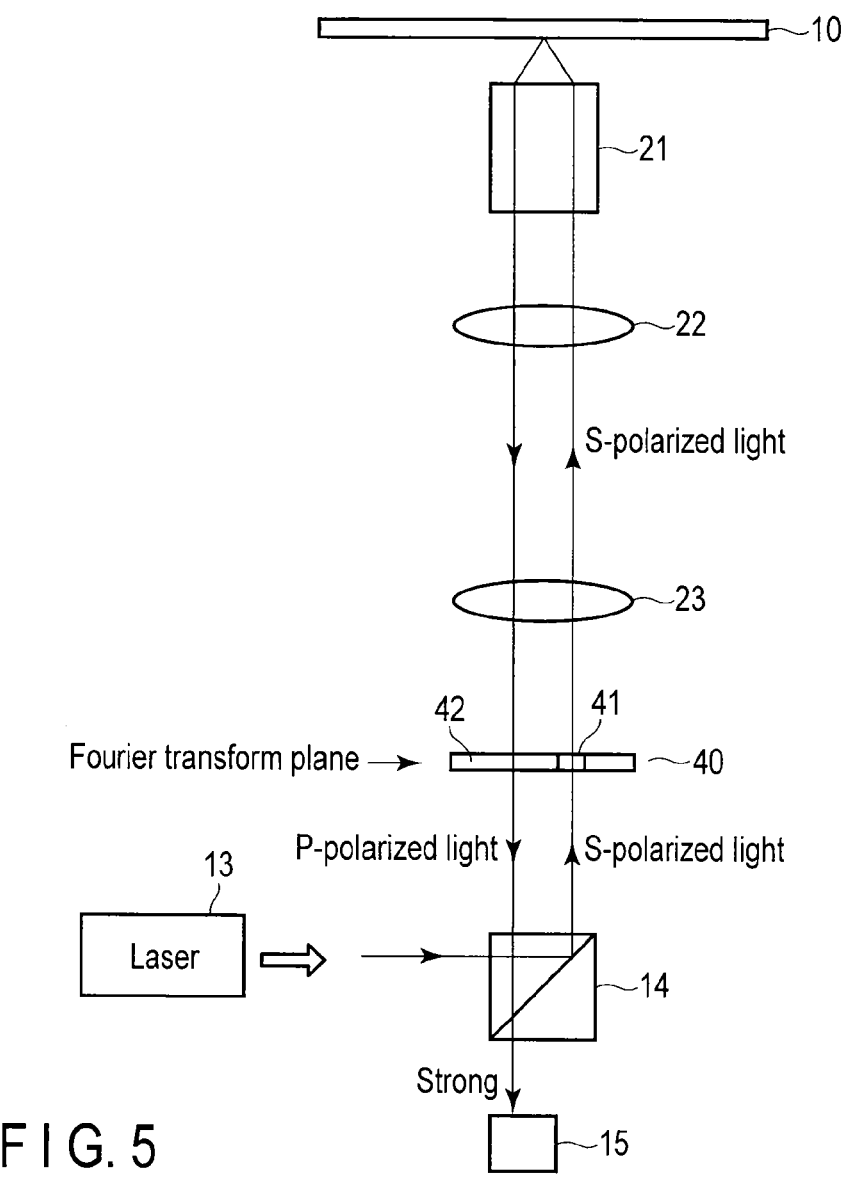
FIG. 5 is a diagram illustrating an optical structure of a pattern test apparatus according to a second embodiment.

FIG. 5 is a diagram illustrating an optical structure of a pattern test apparatus according to a second embodiment. The constituent elements which are the same as those in FIG. 3 are denoted by the same respective reference numerals, and detailed explanation thereof is omitted.

The present embodiment is different from the first embodiment explained above, in that testing is by means of linearly, not circularly, polarized light.

Figure 6:
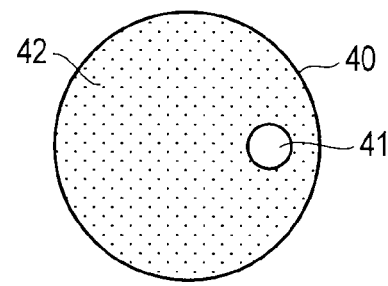
FIG. 6 is a plan view illustrating a structure of a polarizing controller used for the pattern test apparatus of FIG. 5.

In the present embodiment, as illustrated in FIG. 6, a polarizing controller 40 provided in the Fourier transform plane of a photomask 10 includes an illumination light passage region (first region) 41 which is transparent (blank glass). A second region 42, which is the other part of the polarizing controller 40, is a half-wave plate, in which a crystal orientation has an angle of 45° with respect to an X-axis, when the X-axis corresponds to a direction of light made incident on the PBS 14 from the light source, a Z-axis corresponds to a direction of light reflected from the PBS 14 and going toward the photomask, and a Y-axis corresponds to a direction perpendicular to both the X- and Z-axes. Specifically, the retardation of the first region 41 of the polarizing controller 40 is 0°, and the retardation of the second region 42 is 180°.

The illumination light from a light source 13 is linearly polarized light (S-polarized light). The illumination light is reflected by the PBS 14, and obliquely applied to the surface of the photomask 10 by the optical system 20. The light reflected by the surface of the photomask 10 is extracted by the optical system 20, and returns to the Fourier transform plane. Since the half-wave plate is provided in the most part (second region 42) of the Fourier transform plane, the reflected light is changed into P-polarized light, passes through a PBS 14, and detected by a photodiode array 15. Thus, the efficiency of detection of the reflected light is improved.

As described above, according to the present embodiment, since the polarizing controller 40 is disposed in the Fourier transform plane of the photomask 10, even the first region 41 having a small area can guide test light of sufficient amount to the mask. In addition, the reflected light from the photomask 10 can be extracted through the second region 42 having an area greater than the first region 41. Thus, the same effect as that of the first embodiment is obtained. Besides, it is possible to improve the reflection light detection efficiency in linearly polarized light illumination, which is impossible in prior art.

The polarizing controller 40 may have a structure, in which the first region 41 is formed of a half-wave plate having a crystal axis orientation of 45°, and the second region 42 is formed of blank glass, which is contrary to the above explanation. This structure can also improve the transmission efficiency of the PBS 14.

(Third Embodiment)

Figure 7:
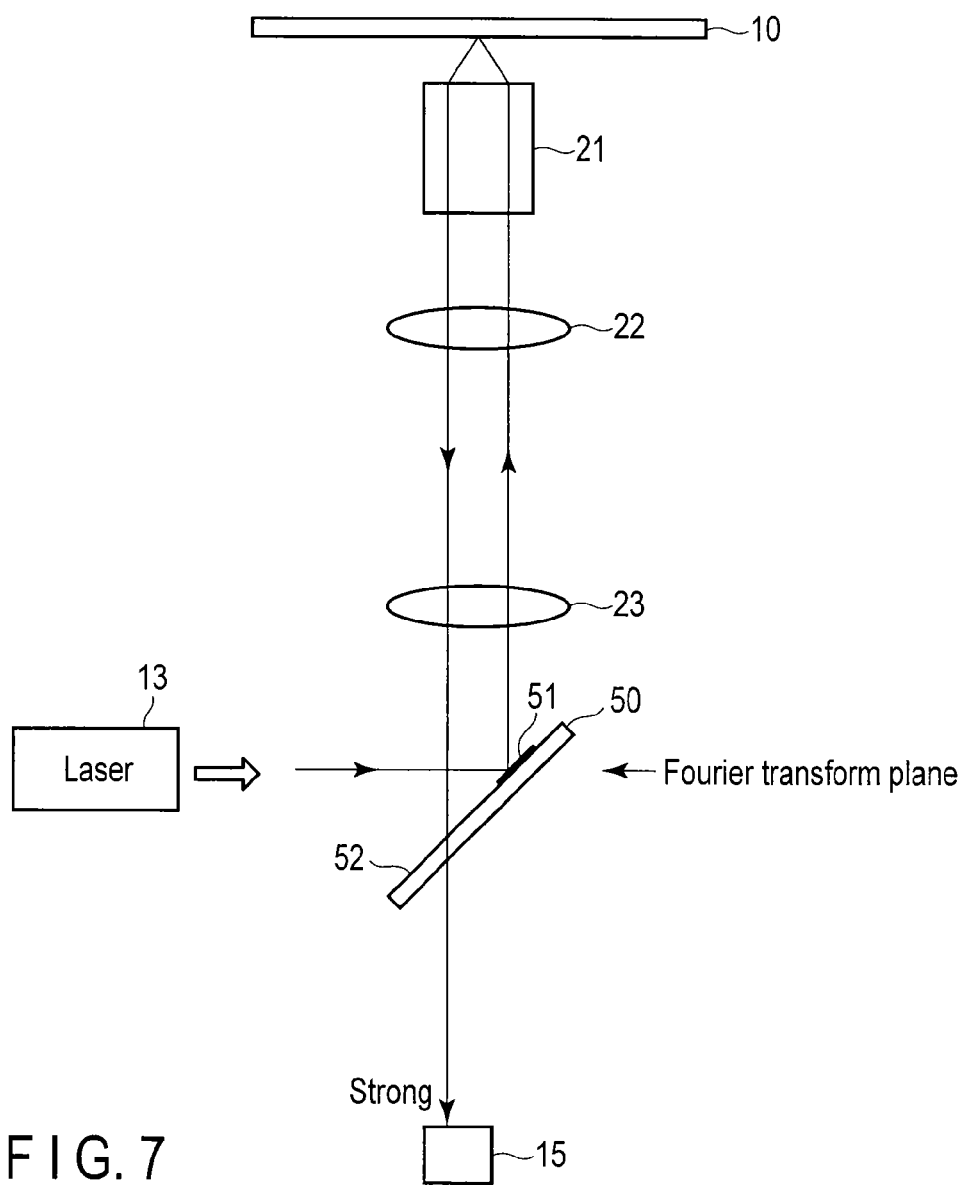
FIG. 7 is a diagram illustrating an optical structure of a pattern test apparatus according to a third embodiment.

FIG. 7 is a diagram illustrating an optical structure of a pattern test apparatus according to a third embodiment. The constituent elements which are the same as those in FIG. 3 are denoted by the same respective reference numerals, and detailed explanation thereof is omitted.

The present embodiment is different from the first embodiment explained above, in that reflected light from a photomask is extracted without using a PBS.

Figure 8:
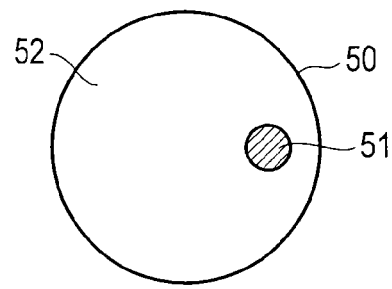
FIG. 8 is a plan view illustrating a structure of a partial reflector used for the pattern test apparatus of FIG. 7.

A partially reflecting mirror 50 is disposed in a Fourier transform plane of a photomask 10. Specifically, the partially reflecting mirror 50 is disposed in a pupil position or a pupil conjugate position of an objective lens 21. As illustrated in FIG. 8, the partially reflecting mirror 50 is obtained by providing part of a transparent glass 52 with a totally reflecting mirror 51. The partially reflecting mirror 50 is disposed at an angle of 45° with respect to an incident direction of the illumination light and the surface of the photomask 10. Only a region of the partially reflecting mirror 50, on which the illumination light from the light source 13 is made incident, is formed of the totally reflecting mirror 51.

Since the most part (region excluding the totally reflecting mirror 51) of the partially reflecting mirror 50 is transparent, it is not always necessary to use the transparent glass 52. For example, the Fourier transform plane may be provided with only the minute totally reflecting mirror 51.

The illumination light from the light source 13 may be circularly polarized light or linearly polarized light. The illumination light is reflected by the totally reflecting mirror 51, and obliquely made incident on the surface of the photomask 10 by the optical system 20. The reflected light from the surface of the photomask 10 is extracted by the optical system 20, and dislocated from the position of the totally reflecting mirror 51 in the Fourier transform plane. Then, the light which has transmitted through the partially reflecting mirror 50 is detected by a photodiode array 15.

As described above, according to the present embodiment, the Fourier transform plane is provided with the partially reflecting mirror 50, and thereby testing does not require an expensive optical component such as a PBS. In addition, when circularly polarized light is used as illumination light, it is possible to prevent a reduction in the amount of light because of the influence of form birefringence, and so improve the test accuracy, even when the test pattern has a periodic structure smaller than the wavelength. Besides, when linearly polarized light is used as illumination light, it is possible to improve the reflected light detection efficiency in linearly polarized light illumination, which is impossible in prior art.

(Modification)

The present invention is not limited to the above embodiments.

In the first and second embodiments, the illumination light is reflected by the PBS and guided to the mask, and the light reflected from the photomask is transmitted through the PBS and guided to the sensor. The illumination light may be transmitted through the PBS and guided to the mask, and the light reflected from the photomask may be reflected by the PBS and guided to the sensor, which is contrary to the first and second embodiments. For example, P-polarized light may be used as illumination light made incident on the PBS from the light source, and the light reflected from the photomask may be changed into S-polarized light before it is made incident on the PBS.

In the third embodiment, the partially reflecting mirror has a structure, in which the small first region which lets the illumination light pass through is formed of a reflecting mirror, and the second region is transparent. The small first region may be transparent, and the second region may be formed of a reflecting mirror, which is contrary to the third embodiment. In this case, the illumination light is let pass through the first region, and the light reflected by the reflecting mirror of the second region is detected by the sensor.

Although the embodiments show the case of using a photomask as a test sample, the present invention is not limited to it, but may be applied to a nano-imprint lithography (NIL) mask. The present invention is also applicable to pattern defect test for semiconductor wafers and liquid crystal substrates. Although the embodiments show the case where the first region is formed in a position shifted from the optical axis of the lens, the present invention is not limited to it, but the first region may be provided in the center of the optical axis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pattern test apparatus which tests pattern defects by using a pattern image obtained by applying light to a test sample, comprising:
    a light source configured to apply test light of a predetermined wavelength to the test sample;
    a polarizing beam splitter which reflects the light from the light source, and guides the light onto the test sample;
    an imaging device which receives light which has been reflected by the test sample and reflected by the polarizing beam splitter;
    an optical system which forms a Fourier transform plane of the test sample between the test sample and the polarizing beam splitter; and
    a polarizing controller disposed in the Fourier transform plane, the polarizing controller including a first region which lets the test light through, and a second region which has an area greater than that of the first region and lets the light reflected by the test sample through, the first region and the second region having different retardation quantities.

2. The apparatus of claim 1, wherein the retardation of the first region of the polarizing controller is 90°, and the retardation of the second region is obtained by shifting the retardation from 90° by change in a polarized state obtained by birefringence in the test sample.

3. The apparatus of claim 1, wherein the retardation of the first region of the polarizing controller is 0°, and the retardation of the second region is 180°.

4. The apparatus of claim 1, wherein the retardation of the first region of the polarizing controller is 180°, and the retardation of the second region is 0°.

5. The apparatus of claim 1, wherein the first region is disposed such that the light which has passed the first region is made incident on a surface of the test sample at an inclined angle.

6. The apparatus of claim 1, further comprising:
a comparison circuit which compares measured image data obtained by the imaging device with design image data obtained from design data used for formation of a pattern of the test sample, and determines that a defect exists if the compared data items do not agree.

7. The apparatus of claim 1, wherein the optical system is formed of an objective lens which is opposed to a surface of the test sample, and a relay lens which is disposed in a position facing a side of the objective lens, the side not facing the test sample.

8. The apparatus of claim 1, wherein the polarizing controller is formed to have a disk shape, the first region is a circular region located in a position shifted from an optical axis of the optical system, and the second region is a region excluding the first region in the polarizing controller.

* * * * *